United States Patent [19]

Soda et al.

[11] 4,071,405

[45] Jan. 31, 1978

[54] METHOD OF PRODUCING SULFUR CONTAINING L-AMINO ACIDS

[75] Inventors: Kenji Soda, Uji; Hidehiko Tanaka, Kyoto; Hidetsugu Nakazawa; Koji Mitsugi, both of Yokohama, all of Japan

[73] Assignee: Ajinomoto Co., Inc., Tokyo, Japan

[21] Appl. No.: 696,398

[22] Filed: June 15, 1976

[30] Foreign Application Priority Data

June 19, 1975 Japan .................................. 50-73774

[51] Int. Cl.$^2$ ............................................. C12D 13/06
[52] U.S. Cl. ...................................................... 195/29
[58] Field of Search ........................................... 195/29

[56] References Cited

PUBLICATIONS

Journal of Biochemistry; vol. 78, pp. 1105–1107; 1975.

*Primary Examiner*—Lionel M. Shapiro
*Assistant Examiner*—Robert J. Warden
*Attorney, Agent, or Firm*—Cooper, Dunham, Clark, Griffin & Moran

[57] ABSTRACT

Method for the production of substituted sulfur containing L-amino acids by contacting $\beta$- or $\gamma$-substituted amino acids in an aqueous medium containing methioninase together with the precursor of the substituent.

6 Claims, No Drawings

METHOD OF PRODUCING SULFUR CONTAINING L-AMINO ACIDS

THE INVENTION

This invention relates to methods for the production of L-amino acids such as L-cysteine, L-homocysteine and their S-substituted derivatives.

Sulfur-containing amino acids in which the sulfur atom is attached to the β- or γ-position of the aliphatic chain are a well known class of compounds useful for many purposes. Certain of them, for example, are known for their physiological activities. Some are useful as additives to standard mammalian diets wither because of inherent nutritive value or as flavor producers or enhancers. They are useful intermediates in the synthetic production of therapeutic agents. They also may be utilized for study and analysis, particularly by comparison of their physiological activities with the activities of other materials. There is therefore a need for methods of producing such compounds on both experimental and commercial scales.

It has now been discovered, in accordance with this invention, that substituted sulfur-containing L-amino acids in which the sulfur is attached to a β- or γ-carbon atom can be produced by contacting a precursor amino acid in an aqueous medium containing methioninase and a precursor of the substituent. More specifically, methods have been discovered by which γ-substituted sulfur derivatives of γ-substituted-α-amino butyric acid.

The term "substituted sulfur containing L-amino acid" as used in this specification and claims in describing the L-amino acids produced by the process means that in the amino acid produced there is a sulfur attached to the β- or γ-carbon atom, and that this sulfur is itself substituted with another atom such as hydrogen or a group such as phenyl.

The process of the invention is carried out by contacting β- or γ-substituted L-amino acid in an aqueous medium containing methioninase in the presence of the precursor of the substituent.

A wide variety of sulfur-containing chemical compounds can be employed as substituent precursors in the practice of this invention. Generally they may be defined as sulfur-containing compounds containing an active hydrogen having at least one unshared electron pair associated with the sulfur atom. In the course of the reaction the entire molecule, with the exception of the active hydrogen becomes bonded to the original β- or γ-substituted amino acid through union of the sulfur atom with the β- or γ-carbon atom. The active hydrogen joins with the original β- or γ-substituent to form a molecular by-product. In a sense, the reaction is a nucleophilic displacement reaction in which the substituent precursor, minus the active hydrogen atom functions as the nucleophile.

The sulfur containing compounds useful in the practice of this invention may be represented by the generic formula:

$$Y-H$$

wherein Y is a sulfur containing, nucleophilic moiety in which there is at least one unshared electron pair associated with the sulfur atom.

Typical of the compounds which can be employed as substituent precursors in the practice of this invention are hydrogen sulfide and disulfide, sulfurous acid; thiols such as alkyl, alkenyl, aryl and aralkyl mercaptans; sulfenic acids including alkyl, alkenyl, aryl and aralkyl sulfenic acids; and sulfinic acids including alkyl, alkenyl, aryl and aralkyl sulfinic acids. In these compounds, preferably, alkyl and, alkenyl radicals may contain up to six carbon atoms, and aryl and aralkyl radicals may contain up to twelve carbon atoms, and may be substituted with reaction inert substituents.

Specific compounds which may be employed include cysteine thiol, cysteine, homocysteine, cysteine sulfenic acid, homocysteine sulfenic acid, homocysteine sulfinic acid, propyl mercaptan, phenyl mercaptan, ortho methyl phenyl mercaptan, benzyl mercaptan, α-naphthyl mercaptan, hexyl mercaptan, hexenyl mercaptan, phenyl sulfenic acid, paraethyl phenyl sulfinic acid and α-thio-β-methyl naphthalene. Other typical compounds are illustrated in the examples.

The amino acid starting compounds which may be used in the process of this invention may be represented by the generic formula:

$$X(CH_2)_n CH(NH_2)COOH$$

wherein $n$ is 1 or 2.

They are therefore β-substituted alanines or γ-substituted-α-amino acids. X may be any of a wide variety of substituents, many of which are illustrated in the examples.

The characterizing feature, however, by which those skilled in the art can recognize the alanine or α-aminobutyric acid derivative as one which can be usefully employed in this invention is that, if useful, it can be converted to XH, ammonium ion and either pyruvic acid or α-keto butyric acid when held with methioninase in an aqueous medium.

Thus the utility of a compound as a starting compound can be determined by holding the compound as a concentration of about 0.5 g/dl for about 16 hours at about 25° C to 30° C in an aqueous medium containing 1 g/dl $KH_2PO_4$, 2 g/dl $K_2HPO_4$, 0.001 g/dl pyridoxal phosphate and 0.5 g/dl freeze dried cells of Pseudomonas ovalis IFO 3738.

Of course, other known sources of methioninase, or methioninase preparations of varying degrees of purity can be employed, as will be apparent to those skilled in the art.

The presence of α-keto butyric acid in the aqueous solution can be determined by the known MBTH method which employs 3-methyl-2-benzothiazolone hydrazine as the test reagent, Agr. Biol. Chem. (Japan) 31, 1054 (1967). Pyruvic acid can be determined by the method of Friedeman T.E. and Haugen, G.E. J. Biol. Chem. 147, 415-442, (1943).

Typically useful substituents which may be represented by X include those represented by halogen, and by $R_1O-$, $R_2S-$, $R_2SO-$, $R_2SO_2-$, and $HSO_3$ wherein $R_1$ is hydrogen, acyl, alkyl, aryl and aralkyl, and $R_2$ is hydrogen, alkyl, aryl, aralkyl, HOOC $CH(NH_2)CH_2S-$, or HOOC $CH(NH_2)CH_2CH_2S-$. In these definitions alkyl, aryl and aralkyl have the same meaning as above, and acyl refers to substituents, including formyl, containing up to about five carbon atoms.

Methioninase (methionine-α-deamino-γ-mercaptomethanelyase) is a known enzyme which decomposes L-methionine to methylmercaptan, ammonium ion and α-keto butyric acid. The enzyme is known to be produced by various microorganisms such as *Clostridium sporogenes* (Cance. Research 33, 1862-1865), *Eschericia* coli (Medical Journal of Osaka University 2, 111-117), *Pseudomonas ovalis, Pseudomonas taetrolens, Pseudomonas striata* and *Pseudomonas desmolytica* (Summary of Report for the Annual Meeting of Agricultural Chemical Society of Japan 96, 1974). It can be isolated from these sources by known methods.

For the practice of this invention methioninase can be used in various forms including purified or crude methioninase preparations, intact cells of the microorganism which contain the methioninase activity, freeze-dried cells of the microorganism, cells of the microorganism which have been dehydrated with acetone, homogenates of cells of the microorganism, sonicates of the cells of the microorganism.

The aqueous reaction medium contains the enzyme or the enzyme source, the amino acid of formula I and Y-H, and, typically, pyridoxal phosphate and/or inorganic ions.

The preferred concentration of the amino acid of formula I in the reaction mixture is from 0.1 to 20%, and the concentration of Y-H is usually less than 10%. The substituent precursor may be utilized in the form of a salt, preferably an alkali metal salt such as potassium or sodium.

The reaction temperature is preferably maintained at from 1° to 70° C. During the reaction, the pH of the reaction mixture is maintained at from 5 to 12. When the reaction is carried out for 1 to 40 hours, high yields of the sulfur-containing L-amino acid of this invention are accumulated in the reaction mixture.

The sulfur-containing L-amino acid in the reaction medium can be recovered by any known method such as precipitating at a pH of isoelectric point.

EXAMPLE 1

An aqueous culture medium was prepared containing, per deciliter, 0.25 g L-methionine, 0.1 g peptone, 0.2 g glycerine, 0.1 g $KH_2PO_4$, 0.1 g $K_2HPO_4$, 0.01 g $MgSO_4 \cdot 7 H_2O$, and 0.025 g yeast extract, adjusted to pH 8.0 with NaOH, of which 1,000 ml was placed in a 2,000 ml shaking flask, and heated by steam.

Each of the microorganisms shown in Table 1 was inoculated into a shaking flask, and cultured at 27° C for 24 hours. Cells in the resultant culture broth were collected by centrifuging, and freeze-dried.

Aqueous reaction media were prepared containing 32 mM of the amino acid shown in Table 1, 50 mM n-propyl mercaptan, 0.01 mM pyridoxal phosphate and 0.5 g/dl of the freeze-dried cells, and 10 ml portions of each mixture were placed in 500 ml shaking flasks, and shaken at 37° C for 16 hours.

Molar yields of propylthio substituted L-amino acid accumulated in the resultant reaction media were determined and are shown in Table 1.

TABLE 1

| Amino acid | Microorganism | Molar yield (%) |
| --- | --- | --- |
| L-homocysteine | *Pseudomonas taetrolens* IFO 3460 | 20 |
|  | *Pseudomonas ovalis* IFO 3738 | 75 |
|  | *Pseudomonas striata* IFO 12996 | 60 |
|  | *Pseudomonas desmolitica* IFO 12570 | 51 |
| L-γ-chloro-α-amino butyric acid | IFO 3460 | 28 |
|  | IFO 3738 | 85 |
|  | IFO 12996 | 60 |
|  | IFO 12570 | 50 |
| L-methionine | IFO 3460 | 25 |

TABLE 1-continued

| Amino acid | Microorganism | Molar yield (%) |
| --- | --- | --- |
|  | IFO 3738 | 80 |
|  | IFO 12996 | 63 |
|  | IFO 12570 | 57 |

EXAMPLE 2

The aqueous culture medium of Example 1 (40 l) was placed in a 50l fermentor, and sterilized. One liter of a culture broth of *Pseudomonas ovalis* prepared in the manner similar to the method shown in Example 1 was transferred to the fermentor. Cultivation was carried out at 27° C for 24 hours.

The cells in the resultant broth were collected by centrifugation. All of the cells obtained were suspended in 5 liters of a 0.01 M phosphate buffer containing $10^{-5}$ M pyridoxal phosphate and 0.01% mercaptoethanol, at pH 7.2, and the cells suspension was homogenized.

Purified methioninase preparations were obtained from the homogenized mixture through salting-out with ammonium sulfate, DEAE-cellulose chromatography, and hydroxyapatite chromatography, according to the usual procedures.

An aqueous reaction medium was prepared containing 20 mM of the amino acid shown in Table 2, 50 mM ethylmercaptan, and 0.01 mM pyridoxal phosphate, and adjusted to pH 8.0 with KOH. 10 Ml of the aqueous reaction media were mixed with 0.5 mg of the purified methioninase preparation, and shaken at 37° C for 16 hours.

The sulfur-containing L-amino acid produced in the reaction media was isolated and purified using an ion-exchange resin, "Amberlite 1R-120" (H±), and identified by comparison with authentic samples.

Molar yields in Table 2 are the yield of ethionine from L-isomer of the amino acid shown in Table 2.

TABLE 2

| Amino acid ($X-(CH_2)_n-CH(NH_2)-COOH$) | Molar yield (%) |
| --- | --- |
| DL-γ-fluoro-α-amino-butyric acid | 70 |
| L-γ-cloro-α-amino-butyric acid | 95 |
| DL-γ-bromo-α-amino-butyric acid | 83 |
| DL-γ-iodo-α-amino-butyric acid | 13 |
| DL-β-fluoro-alanine | 30 |
| L-β-chloro-alanine | 55 |
| DL-β-bromo-alanine | 21 |
| DL-β-iodo-alanine | 8 |
| L-O-formyl-homoserine | 10 |
| L-O-acetyl-homoserine | 20 |
| L-homoserine | 81 |
| L-O-methyl-homoserine | 55 |
| L-O-phenyl-homoserine | 45 |
| L-O-benzyl-homoserine | 85 |
| L-O-formyl-serine | 12 |
| L-O-acetyl-serine | 10 |
| L-azaserine | 8 |
| L-serine | 67 |
| L-O-methylserine | 63 |
| L-O-ethylserine | 62 |
| L-O-phenylserine | 25 |
| L-O-benzylserine | 31 |
| DL-homocysteine | 75 |
| DL-homocysteinesulfenic acid | 13 |
| DL-homocysteinesulfinic acid | 24 |
| DL-homocysteinesulfonic acid | 30 |
| L-methionine | 92 |
| DL-methioninesulfoxide | 42 |
| DL-methionine sulfone | 74 |
| DL-methionine sulfoximine | 30 |
| L-cystine | 12 |
| L-cysteinesulfinic acid | 10 |
| L-cysteic acid | 8 |
| L-S-methyl-cysteine | 67 |

EXAMPLE 3

The purified methioninase preparation (0.1 mg) was added to 1 ml of an aqueous reaction medium containing 20 mM of the amino acid shown in Table 3, 0.2 g/dl $Na_2SO_3$, 50 mM of the sulfur-containing compound shown in Table 3, 0.01 mM of pyridoxal phosphate, of pH 8.0 (KOH). The aqueous reaction mixture was shaken at 37° C for 16 hours.

Ten μl of the resultant reaction medium was spotted on silica-gel thin layer plate, and developed with a solvent containing 40 parts isobutyl alcohol, 20 parts methyl-ethyl ketone, 20 parts methanol, 1 part water, 14 parts concentrated ammonia water and 5 parts acetone.

$R_f$ of the ninhydrin positive spot on the plate was identical with that of the authentic sulfur-containing L-amino acid shown in Table 3.

The presence of radioisotopes in $S^{35}$-L-methionine and $S^{35}$-L-cysteine was confirmed by liquid-scintillation counter.

Ten μl of 20 mM, 15 mM, 10 mM, 5 mM or 1 mM of L-methione solution were also spotted on the same silica-gel plate, and the color developments of the sulfur-containing L-amino acids were compared with the spots of L-methionine. The symbols in the last column show that the degree of color development of the sulfur-containing L-amino acid were close to that of 20 mM to 15 mM L-methionine, 15 mM to 10 mM L-methionine, 10 mM to 5 mM L-methionine and 5 to 1 mM L-methionine, respectively.

In a manner analogous to that mentioned above, L-methionine, γ-chloro-α-amino butyric acid, and γ-methoxy-α-amino butyric acid were contacted each with thiocysteine, γ-cresol, thioacetic acid, thioglycolic acid and thiolactic acid. Rf of the ninhydrin positive spot of the compounds produced were different from L-methionine, γ-chloro-α-amino butyric acid, and γ-methoxy-α-amino butyric acid, and thus new amino acids were produced.

TABLE 3

| Amino acic used | Sulfur-containing compound used | Sulfur-containing -L-amino acid produced | Amount of product in reaction solution |
|---|---|---|---|
| L-γ-chloro-α-amino butyric acid | methyl mercaptan | L-methionine | ++++ |
| | $S^{35}$-methyl mercaptan | $S^{35}$-L-methionine | ++++ |
| | Methyl sulfinic acid | L-methionine sulfone | +++ |
| | ethyl mercaptan | L-ethionine | ++++ |
| | propyl mercaptan | L-propionine | +++ |
| | isopropyl mercaptan | S-isopropyl-L-homocysteine | ++ |
| | n-butyl mercaptan | S-butyl-L-homocysteine | +++ |
| | tert-butyl mercaptan | S-tert-butyl-L-homocysteine | ++ |
| | sec-butyl mercaptan | S-sec-butyl-L-homocysteine | ++ |
| | thiophenol | S-phenyl-L-homocysteine | ++ |
| | benzyl mercaptan | S-benzyl-L-homocysteine | +++ |
| | β-mercaptoethanol | S-(β-hydroxyethyl)-L-homocysteine | + |
| | cysteamine | S-(β-aminoethyl)-L-homocysteine | + |
| | β-mercaptopropionic acid | S-(β-carboxyethyl)-L-homocysteine | + |
| | dithiothreitol | γ-dithiothreitoyl-L-α-amino-butyric acid | + |
| | methyl sulfenic acid | L-methioninesulfoxide | ++ |
| | methane sulfinamide | L-methioninesulfoximine | + |
| | sodium sulfide | L-homocysteine | + |
| | hydrogen persulfide | L-homocysteine thiol | + |
| L-β-chloroalanine | sodium sulfide | L-cysteine | ++ |
| | $S^{35}$-sodium sulfide | $S^{35}$-L-cysteine | ++ |
| | methyl mercaptan | S-methyl-L-cysteine | +++ |
| | benzyl mercaptan | S-benzyl-L-cysteine | ++ |
| | cysteamine | S-(β-aminoethyl)-L-cysteine | ++ |
| | propenylsulfenic acid | S-propenyl-L-cysteine sulfoxide | + |
| | β-carboxy-isopropyl-mercaptan | S-(β-carboxyisopropyl)-cysteine | + |
| | allyl mercaptan | S-allyl-L-cysteine | ++ |
| | $H_2N$—C(O)SH | S-carbamyl-L-cysteine | + |
| | hydrogen persulfide | L-cysteine thiol | + |
| | sulfurous acid | L-cysteic acid | + |
| L-homoserine | $S^{35}$-methyl mercaptan | $S^{35}$-L-methionine | ++++ |
| | methyl sulfenic acid | L-methionine sulfone | ++ |
| | ethyl mercaptan | L-ethionine | ++++ |
| | propyl mercaptan | L-propionine | ++ |
| | isopropyl mercaptan | S-isopropyl-L-homocysteine | + |
| | n-butyl mercaptan | S-butyl-L-homocysteine | +++ |
| | tert-butyl mercaptan | S-tert-butyl-L-homocysteine | + |
| | sec-butyl mercaptan | S-sec-butyl-L-homocysteine | + |
| | thiophenol | S-phenyl-L-homocysteine | ++ |
| | benzyl mercaptan | S-benzyl-L-homocysteine | +++ |
| | β-mercaptoethanol | S-(β-hydroxyethyl)-L-homocysteine | + |
| | cysteamine | S-(β-aminoethyl)-L-homocysteine | + |
| | β-mercaptopropionic acid | S-(β-carboxyethyl)-L-homocysteine | + |
| | dithiothreitole | γ-dithiothreitoyl-L-α-amino butyric acid | + |
| | methyl sulfenic acid | L-methionine sulfoxide | + |
| | methane sulfinamide | L-methionine sulfoximine | + |
| L-O-methyl-serine | $S^{35}$-hydrogen sulfide | $S^{35}$-L-cysteine | ++ |
| | methyl mercaptan | S-methyl-L-cysteine | ++ |
| | benzyl mercaptan | S-benzyl-L-cysteine | ++ |
| | cysteamine | S-(β-aminoethyl)-L-cysteine | + |
| | propenyl sulfenic acid | S-propenyl-L-cysteine sulfoxide | + |
| | allyl mercaptan | S-allyl-L-cysteine | ++ |
| | $H_2N$—C(O)SH | S-carbamyl-L-cysteine | + |
| L-methionine | $S^{35}$-methyl mercaptan | $S^{35}$-L-methionine | ++++ |
| | methyl sulfinic acid | L-methionine sulfone | +++ |
| | ethyl mercaptan | L-ethionine | ++++ |
| | propyl mercaptan | L-propionine | +++ |
| | isopropyl mercaptan | S-isopropyl-L-homocysteine | ++ |

TABLE 3-continued

| Amino acid used | Sulfur-containing compound used | Sulfur-containing -L-amino acid produced | Amount of product in reaction solution |
|---|---|---|---|
| | n-butyl mercaptan | S-n-butyl-L-homocysteine | +++ |
| | tert-butyl mercaptan | S-tert-butyl-L-homocysteine | ++ |
| | sec-butyl mercaptan | S-sec-butyl-L-homocysteine | ++ |
| | thiophenol | S-phenol-L-homocysteine | ++ |
| | benzyl mercaptan | S-benzyl-L-homocysteine | +++ |
| | β-mercaptoethanol | S-(β-hydroyethyl)-L-homocysteine | + |
| | cysteamine | S-(β-aminoethyl)-L-homocysteine | + |
| | β-mercaptopropionic acid | S-(β-carboxyethyl)-L-homocysteine | + |
| | dithiothreitol | γ-dithiothreitoyl-L-α-amino butyric acid | + |
| | methyl sulfenic acid | L-methionine sulfoxide | ++ |
| | methane sulfinamide | L-methionine sulfoximine | + |
| L-cysteine | $S^{35}$-hydrogen sulfide | $S^{35}$-L-cysteine | +++ |
| | S-methyl mercaptan | S-methyl-L-cysteine | +++ |
| | benzyl mercaptan | S-benzyl-L-cysteine | ++ |
| | cysteamine | S-(β-aminoethyl)-L-cysteine | ++ |
| | propenylsulfenic acid | S-propenyl-L-cysteine sulfoxide | + |
| | allyl sulfenic acid | S-allyl-L-cysteine sulfoxide | ++ |
| | methyl sulfenic acid | S-methyl-L-cysteine sulfoxide | + |
| | β-carboxyisopropyl mercaptan | S-(β-carboxyisopropyl)-cysteine | + |
| | allyl mercaptan | S-allyl-L-cysteine | ++ |
| | $H_2N$—C(O)SH | S-carbamyl-L-cysteine | + |

What is claimed is:

1. A method for the production of substituted sulfur-containing L-amino acids in which the sulfur is attached to the β- or γ-carbon atom of the amino acid, which comprises:

a. contacting a β- or γ-substituted L-amino acid in an aqueous reaction medium containing methioninase together with a sulfur containing compound to accumulate the substituted sulfur-containing L-amino acid in the medium, and b. recovering the substituted sulfur-containing L-amino acid from the medium, the said β- or γ-substituted L-amino acid being characterized as one which is converted to pyruvic or α-keto butyric acid when held in an aqueous medium with methioninase, the said sulfur-containing compound being characterized as one which contains an active hydrogen atom and at least one unshared electron pair associated with the sulfur atom, the substituted sulfur-containing L-amino acid being characterized as one in which the original β- or γ-substitute is replaced by the entire nucleophilic moiety of the sulfur-containing compound which remains after removal of hydrogen therefrom.

2. A method as in claim 1 wherein the β- or γ-substituted L-amino acid is represented by the formula $X(CH_2)_nCH(NH_2)COOH$ in which n is 1 or 2 and X is selected from the group consisting of halogen, $R_1O$-, $R_2S$-, $R_2SO$-, $R_2SO_2$-, and $HSO_3$ wherein $R_1$ is hydrogen, acyl, alkyl, aryl and aralkyl, and $R_2$ is hydrogen, alkyl, aryl, aralkyl, HOOC $CH(NH_2)CH_2S$-, and HOOC $CH(NH_2)CH_2CH_2S$-.

3. A method as in claim 2, wherein said X is halogen.

4. A method as in claim 1, wherein said sulfur-containing compound is selected from the group consisting of hydrogen sulfide and disulfide, sulfurous acid; alkyl, alkenyl, aryl and aralkyl mercaptans; alkyl, alkenyl, aryl and aralkyl sulfenic acids and alkyl, alkenyl, aryl and aralkyl sulfinic acids.

5. A method as in claim 4, wherein said alkyl and alkenyl radicals contain up to six carbon atoms and said aryl and aralkyl radicals contain up to twelve carbon atoms.

6. A method as in claim 1, wherein said methioninase is produced by a microorganism of the genus Pseudomonas.

* * * * *